(12) United States Patent
Brautigam et al.

(10) Patent No.: US 8,642,021 B2
(45) Date of Patent: *Feb. 4, 2014

(54) CONDITIONING COMPOSITION FOR HAIR

(75) Inventors: Ina Brautigam, Darmstadt (DE); Frank Hermes, Seeheim (DE)

(73) Assignee: Kao Germany GmbH, Darmstadt (DE)

( * ) Notice: Subject to any disclaimer, the term of this patent is extended or adjusted under 35 U.S.C. 154(b) by 1520 days.

This patent is subject to a terminal disclaimer.

(21) Appl. No.: 11/001,840

(22) Filed: Dec. 2, 2004

(65) Prior Publication Data

US 2005/0152863 A1    Jul. 14, 2005

(30) Foreign Application Priority Data

Dec. 5, 2003  (EP) .................................... 03027985

(51) Int. Cl.
*A61K 8/00* (2006.01)

(52) U.S. Cl.
USPC .... 424/70.1; 424/70.12; 424/93.1; 424/93.45

(58) Field of Classification Search
USPC ............... 424/70.1, 70.2, 70.4, 70.11, 70.12, 424/70.121, 70.19, 70.21, 70.27, 70.28, 424/70.31, 157.1, 535, 93.1, 93.45
See application file for complete search history.

(56) References Cited

U.S. PATENT DOCUMENTS

| | | | |
|---|---|---|---|
| 3,984,566 A * | 10/1976 | Van Scott et al. | 514/460 |
| 4,035,267 A * | 7/1977 | Gleckler et al. | 132/202 |
| 4,268,500 A | 5/1981 | Cloninger | 424/70 |
| 5,385,743 A * | 1/1995 | Hans van der Schaft | 426/42 |
| 6,635,702 B1 * | 10/2003 | Schmucker-Castner et al. | 524/291 |
| 6,923,954 B2 * | 8/2005 | Doi et al. | 424/70.19 |
| 2005/0074440 A1 * | 4/2005 | Lin | 424/93.45 |

FOREIGN PATENT DOCUMENTS

| | | | | |
|---|---|---|---|---|
| DE | 2630560 | 1/1978 | ............ | A61K 7/48 |
| EP | 0315541 | 5/1989 | ............ | A61K 7/48 |
| FR | 2411001 | 7/1979 | ............ | A61K 7/00 |
| JP | 07327633 A * | 12/1995 | | |
| WO | WO 0028966 A1 * | 5/2000 | | |
| WO | WO 03/070208 A1 | 8/2003 | ............ | A61K 7/134 |

OTHER PUBLICATIONS

Abstract Accession No. 2000:351345 from the CaPlus database on STN, the bibliography, abstract and indexing data for WO 200028966 A1, downloaded on Aug. 8, 2007, 2 pages.*
Quest International: "Yogurtene" Cosmetic Ingredients (Jun. 2000) pp. 1-17.*
Machine translation of JP 07327633 A dowloaded from the JPO Feb. 14, 2012.*
thehealthyeating.org website (www.healthyeating.org/Milk-Dairy/Nutrients-in-Milk-Cheese-Yogurt/Yogurt-Nutrition.aspx?Referer=dairycouncilofca (downloaded Feb. 28, 2013).*
Website: Clairol's Touch of Yoghurt Shampoo (http://brandfailures.blogspot.com/2006/12/other-famous-brand-idea-failures.html) downloaded Feb. 28, 2013).*
Skin Deep website http://www.ewg.org/skindeep/ingredient/702759/GUAR_HYDROXYPROPYLTRIMONIUM_CHLORIDE/downloaded Sep. 29, 2013.*
European Search Report for application No. EP 03 02 7985 dated May 19, 2004.

* cited by examiner

*Primary Examiner* — Susan Hanley
(74) *Attorney, Agent, or Firm* — Norris McLaughlin & Marcus PA

(57) ABSTRACT

The present invention is about conditioning compositions for hair comprising spray dried yoghurt powder and at least one cationic conditioning agent. With the compositions of the present invention hair properties such as smoothness, elasticity, volume and body and shine is improved. According to the present invention the yoghurt powder comprising compositions can be applied to hair as a shampoo, conditioner either leave in and/or rinse off types.

17 Claims, No Drawings

CONDITIONING COMPOSITION FOR HAIR

This invention is about composition for hair with a natural ingredient. Natural ingredient used is yoghurt powder.

Hair care compositions have been found their application for many decades. Although the state of the art is quite well established there is still need for improvements.

Natural ingredients have always been attractive to the consumer. Compositions containing natural ingredients especially derived from the edible ones have always been regarded as safer than any other composition offered mainly based on synthetic raw materials. Designing modern cosmetic formulations solely on the basis of natural ingredients will probably take more time in the future.

In cosmetic magazines, periodicals as well as textbooks, the use of natural ingredients have been shown together with synthetic raw materials. Chemically modified active ingredients gained from natural resources are as well found their applications in cosmetics.

DE 44 29 928 is on the use of gingko extract in skin care compositions for preventing wrinkle formation. Green tea extract containing hair treatment composition is disclosed in DE 197 35 865. The same extract has as well been found to deliver beneficial effects in permanent shaping process including reducing and oxidative treatments of hair (DE 197 49 164).

In a U.S. Pat. No. 4,268,500, use of yoghurt as a natural product for treating scalp and hair is disclosed. Natural yoghurt is used simply by rubbing onto hair and scalp according to the method disclosed therein. The document does not disclose any use of yoghurt or its extracts and its powders in any modern cosmetic formulation.

In recently published PCT application, WO 03/070208, use of yogurt is disclosed for improvement of non-oxidative hair colouring. The disclosure contains as well shampoo and conditioner compositions to be used for improving colour retention on non-oxidatively coloured hair. The document, however does not deal with hair conditioning compositions for hair.

It has surprisingly been found out that by incorporating yoghurt powder into a hair cleansing and/or caring/conditioning compositions such as shampoo, conditioner, rinse off treatment, leave-in treatment, properties of hair is improved dramatically in terms of smoothness, combability, shine, volume and body and elasticity.

Thus, the subject matter of the present invention is providing compositions for hair comprising yoghurt powder and a cationic conditioning ingredient.

It is yet another subject of the present invention that the use of conditioning compositions comprising yoghurt powder and at least one cationic conditioning agent for improving hair properties mentioned above.

Yoghurt powder is a raw material prepared by spray drying of natural yoghurt after completion of fermentation. Yoghurt powder comprises the following major components:
- approximately 53.5% lactose,
- approximately 25% proteins,
- approximately 7.5% lactic acid,
- approximately 5% minerals and trace elements,
- approximately 1% vitamines, and
- approximately 2% lipids.

Compositions of the present invention comprise yoghurt powder in a concentration range of 0.01 to 10%, preferably 0.01 to 5%, more preferably 0.01 to 3 by weight calculated to total composition.

Compositions for hair according to the present invention are any of those well-known types such as shampoo, conditioner, treatment, lotions, and gels. Those compositions used especially after shampooing can be applied to hair either as a leave-in or as a rinse off compositions.

Hair cleansing preparation of the present invention can be in the form of conventional liquid thickened shampoo, as well in the form of ready to use foam delivered either from a pump-foamer or from an aerosol bottle. In the case that an aerosol foam preparation is preferred, propellant gas must be added to the formulation.

Cleansing shampoo composition of the present invention comprises at least one surfactant selected from anionic, non-ionic and/or amphoteric or zwitterionic surfactants at a concentration range of 2 to 60%, preferably 5 to 50% and more preferably 5 to 40% by weight, calculated to the total composition.

Anionic surfactants suitable within the scope of the invention are preferably present in an amount from 1 to about 30%, preferably 2 to 25% and most preferably 2-20% by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_1-(C_2H_4O)_n-O-CH_2COOX,$$

wherein $R_1$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

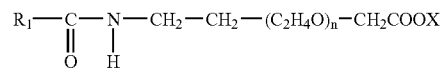

wherein $R_1$ and X have the above meanings, and n is in particular a number from 1 to 10, preferably 2.5 to 5.

Such products have been known for some time and are on the market, for example, under the trade name "AKYPO®" and AKYPO-SOFT®.

Also useful are $C_8$-$C_{20}$-acyl isethionates, alone or in admixture with other anionic surfactants, as well as sulfofatty acids and the esters thereof.

It is also possible to use mixtures of several anionic surfactants, for example, a mixture of an α-olefin sulfonate and a sulfosuccinate, preferably in a proportion of 1:3 to 3:1, or of an ether sulfate and a polyether carboxylic acid or alkyl amidoether carboxylic acid.

An overview of the anionic surfactants used in liquid body cleansing compositions can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the shampoo compositions according to the invention are nonionic surfactants in admixture with anionic surfactants.

These are described in Schrader, l.c., on pages 600-601 and pp. 694-695. Especially suited are alkyl polyglucosides of the general formula

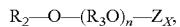

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides in an amount from about 0.25% to about 5%, preferably about 0.5% to about 3.5% by weight, calculated to the total composition.

Such amineoxides are state of the art, for example $C_{12}$-$C_{18}$— alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names Ammonyx®, "Aromox®" or Genaminox®.

Further nonionic surfactants useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the compositions according to the invention can also contain amphoteric or zwitterionic surfactants, for example in an amount from about 0.5% to about 10%, preferably from about 1% to about 7.5% by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

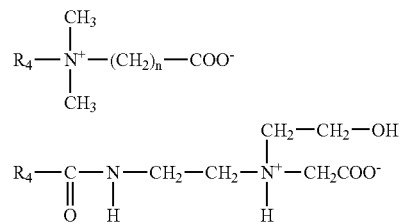

wherein $R_4$ is a $C_8$-$C_{18}$-alkyl group and n is 1 to 3; sulfobetaines of the structure

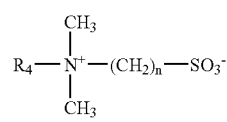

wherein $R_4$ and n are same as above; and amidoalkyl betaines of the structure

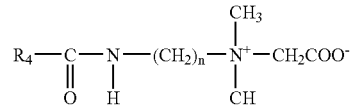

wherein $R_4$ and n are same as above.

Hair conditioning compositions of the present invention can be in the form of either leave in or rinse of emulsions used especially after shampooing. The emulsion type conditioners comprise in addition to yoghurt powder at least one fatty alcohol of the following formula

where $R_5$ is a saturated or unsaturated, branched or non-branched fatty acyl chain with 8-24 C atoms. Concentration of fatty alcohols is usually less than 20%, preferably less than 15% by weight calculated to total composition. Typical examples to the most useful fatty alcohols are myristyl alcohol, palmityl alcohol, cetyl alcohol, stearyl alcohol, behenyl alcohol and their mixtures. As a mixed fatty alcohol the mostly used one is the cetearyl alcohol as well preferred in the compositions of the present invention.

The hair conditioning composition of the present invention comprises surface-active substances as emulsifiers. These can be anionic and/or nonionic and/or cationic and/or amphoteric or zwitterionic and/or their mixtures incorporated at a concentration ranging between 0.1-10%, preferably 0.1-7.5% and more preferably 0.1-5% by weight calculated to the total composition. Preferred emulsifiers are of non-ionic and cationic types and the above-specified concentrations are given for these emulsifiers. The anionic ones are as a rule not preferred and if their presence is desirable because of any reason, those should form the very minor part, as electrostatic interactions with the cationic material can disturb the stability of those conditioners. Zwitterionic ones are the ones preferred to lesser extent. Structural information and examples to the anionic, non-ionic and amphoteric ones are given above for shampoo preparations is as well valid for the emulsion type of conditioners.

The compositions of the present invention comprise cationic hair conditioning agents. Cationic conditioning agents is selected from cationic amphiphilic compounds, cationic polymers and cationic silicone derivatives. The compositions can as well comprise other conditioning agents such as oily substances and non-ionic substances.

Cationic surfactants are useful in the compositions of the present invention as emulsifiers and as conditioning agents at the same time represented with the general formula below:

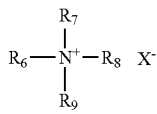

where $R_6$ is a saturated or unsaturated, branched or non-branched alkyl chain with 8-22 C atoms or

where $R_{10}$ is saturated or unsaturated, branched or non-branched alkyl chain with 7-21 C atoms and n has typical value of 0-4 or

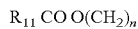

where $R_{11}$ is saturated or unsaturated, branched or non-branched alkyl chain with 7-21 C atoms and n has typical value of 0-4, and $R_7$ is a hydrogen, lower alkyl chain with 1 to 4 carbon atoms, saturated or unsaturated, branched or non-branched alkyl chain with 8-22 C atoms or

where $R_{10}$ is saturated or unsaturated, branched or non-branched alkyl chain with 7-21 C atoms and n has typical value of 0-4 or

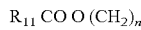

where $R_{11}$ is saturated or unsaturated, branched or non-branched alkyl chain with 7-21 C atoms and n has typical value of 0-4, and $R_8$ and $R_9$ are independent from each other H or lower alkyl chain with 1 to 4 carbon atoms, and X is chloride, bromide or methosulfate.

It should be noted that quaternary ammonium compounds with single alkyl chain are preferred as emulsifiers as well. This should certainly not mean that those are excluded to be used as conditioning ingredients. With the above it is especially stated that the single alkyl chain cationic surfactants have emulsifying ability as well. The others, such as di alkyl dimonium chloride, is more preferred as conditioner as will be explained below. Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stearyl trimonium chloride, dipalmitoyl dimonium chloride, distearyl dimethyl ammonium chloride, stearamidopropyl trimonium chloride, dioleoylethyl dimethyl ammonium methosulfate.

From the above quaternary ammonium compounds disclosed with the general formula, especially preferred are those compounds known per se and are on the market, for example, under the trade names "Schercoquat®", "Dehyquart® F30" and Tetranyl®. Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially preferred are these compounds are known per se and on the market, for example, under the trade name "INCROQUAT® HO" or "OCS". Those compounds known with a general ingredient category under "amodoquat" in the cosmetic industry.

Composition of the present invention comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The cationic polymers also include the quaternized products of graft polymers from organopolysiloxanes and polyethyl oxazolines described in EP-A 524 612 and EP-A 640 643.

Cationic conditioning agents are used alone or in combination with each other. As a results a composition falling in the scope of the present invention can contain for example single cationic polymer as the sole conditioner as well can contain cationic polymer, cationic surfactant and cationic silicone derivative in the same composition as conditioning compounds.

Typical concentration range for cationic conditioners mentioned above can be 0.01-7.5% by weight, preferably 0.05-5% by weight calculated to the total composition.

Oily substances as conditioners according to the present invention are selected from silicone oils either volatile or non-volatile, natural and synthetic oils. Among silicone oils those can be added to the compositions include dimethicone, dimethiconol, polydimethylsiloxane, DC fluid ranges from Dow Corning.

Natural oils suitable are such as olive oil, almond oil, avocado oil, weizenkeim oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof, as well as mineral oils such as paraffin oil and petrolatum.

Lipophilic compounds such as fatty acid esters are as well suitable for the composition of the present invention. Those are such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glyceryl cocoate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula,

$R_{12} CO (O CH_2 CH_2)_n OH$

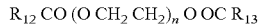

$R_{12} CO (O CH_2 CH_2)_n O OC R_{13}$ where $R_{12}$ and $R_{13}$ are independent from each other saturated, unsaturated or branched or non-branched alkyl chain with 7 to 21 C atoms and n is typically 2-100.

Typical concentration range for any of the additional conditioners mentioned above other than cationic conditioning compounds can be 0.01-15% by weight, preferably 0.05-5% by weight calculated to the total composition.

The compositions according to the invention can also comprise further agents, such as protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed.

Among the natural ingredients in the form of an extract, especially preferred component of the composition according to the invention is green tea extract. This tea extract is obtained from the leaves, leaf buds and tender stems of the tea shrub, *Camellia sinensis* or *Camellia oleifera*, by aqueous or hydro-alcoholic extraction and subsequent spray-drying. In difference to black tea, green tea is a non-fermented product obtained from the *Thea sinensis* or *Thea assamica* species. An overview of the biological and pharmacological effects of green tea and the ingredients thereof can be found, e.g., in an article by A. Pistorius, "Seifen-Öle-Fette-Wachse-Journal", Volume 122., No. 7/1996, pages 468 to 471, to which reference is made. The content of green tea extract is variable in the compositions according to the invention. It preferably ranges from 0.01% to 10%, preferably 0.05% to 5% by weight, calculated to the total composition and the pulverulent extract.

The compositions may contain organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvents in the composition should not exceed 5% by weight. It should be noted that penetration enhancers are useful for both cleansing and after shampoo conditioning preparations. It is obvious that the concentration in the cleansing compositions is usually lower than in the conditioning preparations.

Compositions of the present invention can comprise UV filters either for stabilization of the product colour or for protection of hair from environmental influences such as loss of elasticity, loss of hair colour (bleaching effect of sun light). The UV-absorbing substance is preferably selected from the following compounds:
4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher.

The preferred amount of the UV-absorber ranges from about 0.01% to 2.5%, more preferably from 0.05% to 1% by weight, calculated to the total composition.

Composition of the present invention especially those of cleansing types can be transparent as well a pearly. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in shampoo compositions in crystalline form, i.e. so called pearl-shine agents. The preferred once are PEG-3 distearate and ethylene glycol distearate. The concentration of those can typically be from 0.1 to 3%, preferably 0.5 to 2% by weight, calculated to the total composition.

Solubilizers may be added to the compositions especially when oily substances are chosen as conditioning agents and fragrance oils with highly lipophilic properties. Typical solubilizers may be hydrogenated castor oil known with the trade mark Cremophor RH series from BASF. It should be noted that as well the surfactant mixture can be a good solubilizer for fragrance oils. Typical concentration of the solubilizers can be in the range of 0.01-2% by weight, preferably 0.1-1% by weight, calculated to the total composition. It should be noted without limiting their use that the solubilizers are especially used in the clear cleansing and/or conditioning preparations in order to overcome the turbidity caused by addition of lipophilic materials.

Antidandruff agents such as piroctone olamine (Octopirox), zinc pyrrithion, climbazol can as well be used when an antidandruff effects is targeted. Typical useful concentration range for antidandruff agents is between 0.1-2% by weight calculated to the total composition.

The compositions of the present invention can comprise hair-restructuring agents. The hair restructuring agents preferred are especially the ones disclosed in the German patent DE 197 51 550 C2.

One of the known hair restructuring agents is ceramide type of compound with the general formula

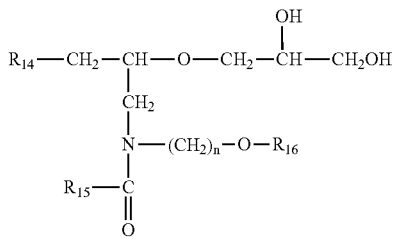

where $R^{14}$ and $R^{15}$ are independent from each other alkyl- or, alkenyl group mit 10 to carbon atoms, $R^{16}$ is methyl, ethyl, n-propyl or isopropyl group and n is a number between 1 to 6, preferably 2 or 3.

Other preferred hair restructuring agents are fatty acids with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2 and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably less than 0.5% by weight calculated to the total weight of the composition. It should be noted without limiting the use of those ingredients the effect of those hair restructuring ingredients is especially elevated when used in combination with penetration enhancers.

The compositions according to the invention can also contain dyestuffs for the direct dyeing of human hair, as so-called tinting or dyeing shampoos and conditioners.

The compositions of the present invention shampoo and after shampoo conditioning compositions can as well be colour-enhancing compositions. In this case, direct dyes are included into the compositions. As direct dyes, cationic and neutral nitro dyes are useful. The use of anionic dyes is as well possible though the color enhancing ability especially at higher end of pH specification is observed to be very low. For shampoo compositions at a low pH range, the acidic dyes can as well be preferred. It is also desirable for the best performance not to use the mixture of acidic and cationic dyestuffs in the same shampoo compositions. The concentration of those dyes is in between 0.0001-5% by weight, preferably 0.0001-2.5% by weight and more preferably 0.0001-1.5% by weight calculated to the total composition.

The useful cationic and neutral nitro dyes, especially preferred in the colouring shampoo and conditioners according to the invention are:

| | |
|---|---|
| Basic Blue 6, | C.I.-No. 51,175; |
| Basic Blue 7, | C.I.-No. 42,595; |
| Basic Blue 9, | C.I.-No. 52,015; |
| Basic Blue 26, | C.I.-No. 44,045; |
| Basic Blue 41, | C.I.-No. 11,154; |
| Basic Blue 99, | C.I.-No. 56,059; |
| Basic Brown 4, | C.I.-No. 21,010; |
| Basic Brown 16, | C.I.-No. 12,250; |
| Basic Brown 17, | C.I.-No. 12,251; |
| Natural Brown 7, | C.I.-No. 75,500; |
| Basic Green 1, | C.I.-No. 42,040; |
| Basic Red 2, | C.I.-No. 50,240; |
| Basic Red 22, | C.I.-No. 11,055; |
| Basic Red 76, | C.I.-No. 12,245; |
| Basic Violet 1, | C.I.-No. 42,535; |
| Basic Violet 3, | C.I.-No. 42,555; |
| Basic Violet 10, | C.I.-No. 45,170; |
| Basic Violet 14, | C.I.-No. 42,510; |
| Basic Yellow 57, | C.I.-No. 12,719. |
| HC Blue No. 2 | |
| HC Blue No. 4 | |
| HC Blue No. 5 | |
| HC Blue No. 6 | |
| HC Blue No. 7 | |
| HC Blue No. 8 | |
| HC Blue No. 9 | |
| HC Blue No. 10 | |
| HC Blue No. 11 | |
| HC Blue No. 12 | |
| HC Blue No. 13 | |
| HC Brown No. 1 | |
| HC Brown No. 2 | |
| HC Green No. 1 | |
| HC Orange No. 1 | |
| HC Orange No. 2 | |
| HC Orange No. 3 | |
| HC Orange No. 5 | |
| HC Red BN | |
| HC Red No. 1 | |
| HC Red No. 3 | |
| HC Red No. 7 | |
| HC Red No. 8 | |
| HC Red No. 9 | |
| HC Red No. 10 | |
| HC Red No. 11 | |

-continued

HC Red No. 13
HC Red No. 14
HC Violet BS
HC Violet No. 1
HC Violet No. 2
HC Yellow No. 2
HC Yellow No. 4
HC Yellow No. 5
HC Yellow No. 6
HC Yellow No. 7
HC Yellow No. 8
HC Yellow No. 9
HC Yellow No. 10
HC Yellow No. 11
HC Yellow No. 12
HC Yellow No. 13
HC Yellow No. 14
HC Yellow No. 15

Suitable anionic dyestuffs are, for example:

| | |
|---|---|
| Acid Black 1, | C.I.-No. 20,470; |
| Acid Blue 1, | C.I.-No. 42,045; |
| Food Blue 5, | C.I.-No. 42,051; |
| Acid Blue 9, | C.I.-No. 42,090; |
| Acid Blue 74, | C.I.-No. 73,015; |
| Acid Red 18, | C.I.-No. 16,255; |
| Acid Red 27, | C.I.-No. 16,185; |
| Acid Red 87, | C.I.-No. 45,380; |
| Acid Red 92, | C.I.-No. 45,410; |
| Acid Orange 7, | C.I.-No. 15,510; |
| Acid Violet 43, | C.I.-No. 60,730; |
| Acid Yellow 1, | C.I.-No. 10,316; |
| Acid Yellow 23, | C.I.-No. 19,140; |
| Acid Yellow 3, | C.I.-No. 47,005; |
| Food Yellow No. 8, | C.I.-No. 14,270; |
| D&C Brown No. 1, | C.I.-No. 20,170 |
| D&C Green No. 5, | C.I.-No. 61,570; |
| D&C Orange No. 4, | C.I.-No. 15,510; |
| D&C Orange No. 10, | C.i.-No 45,425:1; |
| D&C Orange No. 11, | C.I.-No. 45,425; |
| D&C Red No. 21, | C.I.-No. 45,380:2; |
| D&C Red No. 27, | C.I.-No. 45,410:1; |
| D&C Red No. 33, | C.I.-No. 17,200; |
| D&C Yellow No. 7, | C.I.-No. 45,350:1; |
| D&C Yellow No. 8, | C.I.-No. 45,350; |
| FD&C Red No. 4, | C.I.-No. 14,700; |
| FD&C Yellow No. 6, | C.I.-No. 15,985. |

The pH of the compositions according to the invention is in the range of 1.5 to 8, preferably 2 to 7, more preferably 2 to 6. For adjusting the pH of the said compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be chosen in a way that composition reaches the desired pH value as given above. Typically concentration for acids can be 0.01-3% by weight, preferably 0.05-2% by weight, more preferably 0.05-1.5% by weight calculated to the total composition. The pH of the composition can also be adjusted to the required pH by using alkaline solution such as sodium hydroxide, potassium hydroxide or their salts with those acids mentioned above in the case that at the selected acid concentration pH of the composition is lower than that of the aimed value.

The viscosity of the compositions depends on the type of application according to the invention. Compositions for cleansing purposes, conventional shampoos have the viscosity in the range of between about 1000 and about 10,000 mPa·s at 20° C., measured according to Brookfield or Happier at a shear rate of 10 sec$^{-1}$. Whereas cleansing compositions dispensed form an aerosol and/or pump foamer should preferably be very liquid, i.e. viscosity values more than approximately 200 mPa·s measured as given above are not appropriate.

Viscosity of the conditioner or after shampoo compositions can vary largely. Those can be very thick pasty emulsions and as well very liquid compositions to be sprayed onto hair with the aid of a mechanical spray. An aerosol spray composition is as well suitable application form. The after shampoo composition can also be gel type of preparation. Therefore, viscosity of compositions should be chosen appropriately which allows the application onto hair.

In general the compositions of the present invention can be in the form of fully transparent, semitransparent or non-transparent. Transparency should certainly be judged by naked eye in a therefore suitable vessel.

Furthermore compositions of the present invention can comprise all substances customarily found in such preparations.

Examples of such substances are complexing agents, dyestuffs, preservatives, pH-regulants, viscosity regulants such as inorganic salts or polymers to the extent they are not already contained in the initial surfactant mixtures, fragrances, pearl-gloss agents, thickening agents, moisturizers, etc. Furthermore, compositions dispensed from an aerosol preferably do not contain any preservative.

The following examples illustrate the invention.

EXAMPLE 1

| Shampoo Composition for Normal Hair | |
|---|---|
| Sodium lauryl ether sulfate (~2.5EO) | 10.0 |
| | (% by wt.) |
| $C_{12}$–$C_{14}$-alkyl polyglucoside (P.D.: ~1.5) | 3.0 |
| Cocamidopropyl betaine | 4.0 |
| Yoghurt powder | 1.0 |
| Polyquaternium-10 | 0.4 |
| PEG-55-1.2-propyleneglycol oleate | 1.0 |
| Panthenol | 0.3 |
| Sodium chloride | q.s 5.000 mPa · s* |
| Preservative, fragrance | q.s |
| Citric acid | q.s pH 5.0 |
| Water | ad 100.0 |

*measured as given in the description.

Shampoo composition is prepared by combining first the surfactants and other ingredients are added afterwards to the surfactant mixture except that polymer is first dissolved in water before adding to the surfactant mixture.

The shampoo according to the invention developed a full, creamy lather and provided the hair with good wet and dry combability, volume, full and soft body as well as gloss and elasticity. Exclusion of yoghurt powder and cationic polymer is resulted in loss of benefits mentioned above.

EXAMPLE 2

| Shampoo Composition for Fine Hair | |
|---|---|
| Sodium alkyl ether sulfate (~2.5EO) | 6.5 |
| | (% by wt.) |
| $C_{12}$–$C_{14}$-Alkyl polyglucoside (P.D.: ~1.5) | 2.9 |
| Cocoamidopropyl betaine | 1.8 |
| Lauryl hydroxy sultaine | 1.0 |
| Sodium lauroyl glutamate | 1.1 |
| PEG-35-1.2-propyleneglycol cocoate | 2.0 |
| PEG-3-distearate | 0.6 |
| Yoghurt powder | 0.8 |
| Triglycerol | 0.2 |
| Cationic wheat protein hydrolyzate | 0.3 |
| Polyquaternium-6 | 0.3 |
| Aloe extract | 0.1 |
| Perfume, preservative | q.s |
| Water | to 100.0 |

With regard to foaming capability and hair conditioning properties, this shampoo composition basically reflected those of the composition according to Example 1.

EXAMPLE 3

| Shampoo | |
|---|---|
| Sodium lauryl ether sulfate (~2 EO) | 10.5 |
| | (% by wt.) |
| $C_{12}$–$C_{14}$-Alkyl polyglucoside | 2.5 |
| Polyoxyethylene-(55)-1.2-propanediol dioleate | 2.0 |
| Polyquaternium-10 | 0.3 |
| Yoghurt powder | 1.5 |
| Isopropyl myristate | 0.5 |
| PEG-3-distearate | 0.8 |
| Thyme extract | 0.5 |
| Citric acid | q.s. pH 3.5 |
| Lactic acid | 0.1 |
| Glycolic acid | 0.1 |
| Maleic acid | 0.4 |
| Glycerol | 1.0 |
| Perfume, Preservative | 0.3 |
| Water | ad 100.0 |

The shampoo is found to be suitable especially for damaged hair with pores, visual under microscope. After frequent use the pores disappear. After application of the composition hair has high elasticity, intensive shine and smoothness. Yoghurt powder and cationic polymer in the formulation is for obtaining high surface conditioning effect.

EXAMPLE 4

| Anti-Dandruff Shampoo Composition | |
|---|---|
| Sodium lauryl ether sulfate (~2.5EO) | 8.0 |
| | (% by wt.) |
| Disodium lauryl ether sulfosuccinate | 1.0 |
| $C_{12}$–$C_{14}$-Alkyl polyglucoside (P.D.: ~1.5) | 2.5 |
| Cocoamidopropyl betaine | 2.0 |
| Polyquaternium-11 | 0.4 |

| Anti-Dandruff Shampoo Composition | |
|---|---|
| Wheat protein hydrolyzate | 0.5 |
| Yoghurt powder | 0.5 |
| Panthenol | 0.3 |
| Piroctone olamine | 0.4 |
| Citric acid | q.s. to pH 5.5 |
| Perfume, Preservative | q.s |
| Sodium chloride | q.s to 3500 mPa · s* |
| Water | ad 100.0 |

*measured as given in the description.

In addition to an outstanding anti-dandruff effect and excellent foaming properties, this shampoo showed good hair-conditioning properties.

EXAMPLE 5

| Hair treatment composition rinse-off | |
|---|---|
| Cetylstearylalcohol | 5.0 |
| | (% by weight) |
| Di-$C_{12}$–$C_{15}$-alkyldimethylammoniumchlorid | 2.0 |
| Stearyltrimethylammoniumchlorid | 2.0 |
| 1,2-Propandiol | 3.0 |
| Yoghurt powder | 1.0 |
| Ceramide compund according to formula ($R^1$ = $C_{15}H_{31}$; $R^2$ = $C_{16}H_{33}$; $R^3$ = H; $R^4$ = H; n = 2) | 0.2 |
| Benzyloxyethanol | 2.5 |
| Behenic acid | 1.0 |
| Avocadin | 0.2 |
| Fragrance, preservative | q.s. |
| Citric acid/sodium hydroxide | ad pH 5 |
| Wasser | ad 100.0 |

Hair treated with the above formulation is judged to have more elasticity, volume and body and especially excellently high shine. In this formulation hair restructuring ingredients are combined with the caring yoghurt powder and cationic conditioning agents. Exclusion of yoghurt powder and cationic conditioning agents resulted in less smoothness and therefore as well less shine.

EXAMPLE 6

| Spray conditioner - non-aerosol | |
|---|---|
| Ethanol | 45.0 |
| | (Gew.-%) |
| Polyquaternium-6 | 0.1 |
| Yoghurt powder | 0.2 |
| Ceramide compund according to formula ($R^1$ = $C_{15}H_{31}$; $R^2$ = $C_{16}H_{33}$; $R^3$ = H; $R^4$ = H; n = 2) | 0.1 |
| Behenic acid | 0.2 |
| Avocadin | 0.05 |
| PEG-160-hydriertes Ricinusöl | 0.5 |
| Parfum, Konservierungsmittel | q.s. |
| Citronensäure | ad pH 4.7 |
| Wasser | ad 100.0 |

The composition is applied to hair from a common pump spray. Hair treated with the composition has more elasticity, smoothness and shine. Leaving out yoghurt extract and cationic conditioning agent resulted in loss of smoothness and shine. Upon repeated application hair structure improvements are as well observed. This is due to the content of restructuring ingredients.

EXAMPLE 7

| Foam conditioner | |
|---|---|
| Quaternium-80 | 0.2 |
| | (Gew.-%) |
| Polyquaternium-11 | 0.7 |
| Ceramide compund according to formula ($R^1 = C_{15}H_{31}$; $R^2 = C_{16}H_{33}$; $R^3 = H$; $R^4 = H$; n = 2) | 0.2 |
| Behenic acid | 1.0 |
| Yoghurt powder | 0.2 |
| Avocadin | 0.2 |
| PEG-160-hydriertes Ricinusöl | 0.5 |
| Parfum, Konservierungsmittel | q.s. |
| Citronensäure | ad pH 5 |
| Wasser | ad 100.0 |

The composition is filled in an aerosol can at a ratio of 90:10 with commonly used propellant, propane/butane mixture. The composition showed excellent hair conditioning properties. It should be noted that the composition can be used in two different ways, leave-in and rinse off. In leave-in application, amount used is obviously less than in the case of a rinse of application.

EXAMPLE 8

| Colour enhancing shampoo | |
|---|---|
| Cocamido polyether carboxylic acid | |
| (3–4 EO units) sodium salt | 1.0 |
| | (% by wt.) |
| Sodium lauryl ether sulfate (~2.5EO) | 7.0 |
| Polysorbate 20 | 1.0 |
| $C_{12}$–$C_{14}$-Alkyl polyglucoside (P.D.: ~1.5) | 3.0 |
| Cocoamidopropyl betaine | 3.0 |
| Pearl gloss agent (Euperlan PK 900) | 2.0 |
| Cationic cellulose derivative (Polymer JR 400) | 0.5 |
| Yoghurt powder | 0.5 |
| Dimethicone copolyol | 1.0 |
| Basic brown 17 | 0.05 |
| Basic yellow 57 | 0.08 |
| Citric acid | q.s. to pH 5.0 |
| Perfume, Preservative | q.s |
| Sodium chloride | q.s to 3500 mPa · s* |
| Water | ad 100.0 |

Application of this shampoo with its good lather and conditioning properties qualities resulted in a light-blond, glossy hair shade.

EXAMPLE 9

| Hair moisture conditioner composition rinse-off | |
|---|---|
| Cetylstearylalcohol | 4.0 |
| | (% by weight) |
| Cetrimoniumchloride | 2.0 |
| Panthenol | 0.4 |
| Yogurt powder | 1.5 |
| Dimethicone | 0.75 |
| Hydroxypropyl Guar Hydroxypropyltrimonium Chloride | 1.0 |
| Avocado extract | 0.5 |
| Fragrance, preservative | q.s. |
| Citric acid/sodium hydroxide | ad pH 5 |
| Wasser | ad 100.0 |

Hair treated with the above formulation is judged to have more smoothness in wet and dry stage, more elasticity, volume and body and especially excellently high shine. Exclusion of yoghurt powder and cationic conditioning agents resulted in less smoothness and therefore as well as less shine.

EXAMPLE 10

| Hair volume conditioner composition rinse-off | |
|---|---|
| Cetylstearylalcohol | 5.0 |
| | (% by weight) |
| Steartrimonium Chloride | 0.5 |
| Behentrimonium Chloride | 0.4 |
| Yogurt powder | 0.6 |
| DL-Valine | 0.75 |
| Mineral Oil(Paraffinum liquidum) | 0.5 |
| Quaternium-80 | 0.1 |
| Isopropyl Myrisate | 0.3 |
| Bamboo extract | 0.3 |
| Fragrance, preservative | q.s. |
| Citric acid | q.s. pH 4.0 |
| Wasser | add 100.0 |

With the above formulation smoothness and shine of hair is significantly improved compared to a formulation comprising no yoghurt powder and cationic conditioning agents.

EXAMPLE 11

| Spray conditioner for dry hair - non-aerosol | |
|---|---|
| Ethanol | 20.0 |
| | (Gew.-%) |
| Cetrimonium Chloride | 0.8 |
| Yoghurt powder | 0.2 |
| Panthenol | 0.3 |
| Polyquaternium-16 | 0.2 |
| Sunflower extract | 0.3 |
| Parfum, Konservierungsmittel | q.s. |
| Citronensäure | ad pH 4.7 |
| Wasser | ad 100.0 |

The composition showed excellent hair moisturizing properties.

EXAMPLE 12

| Leave in conditioner for colored hair | |
|---|---|
| Dimethicone | 12.0 |
| | (Gew.-%) |
| Polyquaternium-37 | 2.0 |

-continued

| Leave in conditioner for colored hair | |
|---|---|
| Yogurt powder | 0.75 |
| Panthenol | 0.3 |
| Octinoxate/ethylhexyl methoxycinnamate | 0.5 |
| Cetrimonium chloride | 0.3 |
| Caramel | 0.1 |
| Parfum, Konservierungsmittel | q.s. |
| Glyoxylic acid | ad pH 4.7 |
| Wasser | ad 100.0 |

Shine of coloured hair is especially improved with the above formulation. The formulation is especially suitable for leave-in application.

The invention claimed is:

1. A conditioning composition for hair, comprising spray dried yoghurt powder and at least one cationic polymer selected from a Polyquaternium cationic compound or Guar hydroxypropyl trimonium chloride.

2. The conditioning composition according to claim 1, wherein the spray dried yoghurt powder comprises lactose.

3. The conditioning composition according to claim 1, wherein the spray dried yoghurt powder comprises lipids, vitamins and lactic acid.

4. The conditioning composition according to claim 1 wherein the conditioning composition is a cleansing composition and further comprises at least one surfactant selected from the group consisting of anionic, non-ionic, amphoteric and zwitterionic surfactants.

5. The conditioning composition according to claim 4, wherein the cleansing composition comprises (a) anionic surfactant and (b) amphoteric or zwitterionic surfactants at a (a):(b) ratio of 10:1 to 1:1.

6. The conditioning composition according to claim 1 wherein the conditioning composition is an emulsion and comprises at least one fatty alcohol and at least one emulsifier, and is to be applied onto hair after shampooing.

7. The conditioning composition according to claim 1 further comprising conditioning compounds selected from non-ionic and/or oily compounds.

8. The conditioning composition according to claim 1 further comprising a cationic amphiphilic compound selected from a compound according to the formula

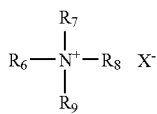

where $R_6$ is a saturated or unsaturated, branched or non-branched alkyl chain with 8-22 C atoms; or $R_{10}\,CO\,NH(CH_2)_n$ where $R_{10}$ is saturated or unsaturated, branched or non-branched alkyl chain with 7-21 C atoms and n has a value of 0, 1, 2, 3 or 4; or $R_{11}CO\,O(CH_2)_n$ where $R_{11}$ is saturated or unsaturated, branched or non-branched alkyl chain with 7-21 C atoms and n has a value of 0, 1, 2, 3 or 4; and $R_7$ is a hydrogen, lower alkyl chain with 1 to 4 carbon atoms, saturated or unsaturated, branched or non-branched alkyl chain with 8-22 C atoms; or $R_{10}\,CO\,NH(CH_2)_n$ where $R_{10}$ is saturated or unsaturated, branched or non-branched alkyl chain with 7-21 C atoms and n has a value of 0, 1, 2, 3 or 4; or $R_{11}\,CO\,O\,(CH_2)_n$ where $R_{11}$ is saturated or unsaturated, branched or non-branched alkyl chain with 7-21 C atoms and n has a value of 0, 1, 2, 3 or 4; and $R_8$ and $R_9$ are independent from each other H or lower alkyl chain with 1 to 4 carbon atoms, and X is chloride, bromide or methosulfate.

9. The conditioning composition according to claim 1, wherein the conditioning composition is a colour enhancing composition and further comprises at least one direct dye.

10. The conditioning composition according to claim 1, comprising yoghurt powder at a concentration of 0.01 to 10% by weight calculated to the total composition.

11. The conditioning composition according to claim 1, comprising cationic conditioning agents at a concentration of 0.01 to 7.5% by weight calculated to the total composition.

12. The conditioning composition according to claim 1 further comprising the ceramide of the formula

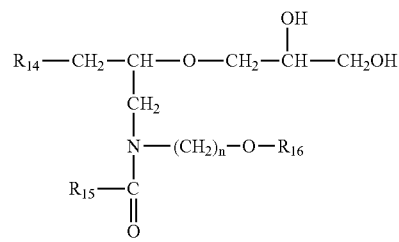

where $R_{14}$ and $R_{15}$ are, independent from each other, alkyl or alkenyl group with 10 to 22 carbon atoms, $R_{16}$ is methyl, ethyl, n-propyl or isopropyl group and n is an integer from 1 to 6.

13. The conditioning composition according to claim 1, further comprising active ingredients selected from the group consisting of anti-dandruff agents, moisturizing agents, and oil soluble or water soluble UV filtering compounds.

14. The conditioning composition according to claim 1, further comprising complexing agents, dyestuffs, preservatives, pH-regulants, viscosity regulants, fragrances, pearl-gloss agents and thickening agents.

15. The conditioning composition according to claim 1 wherein the cationic polymer is selected from the group consisting of Polyquaternium 6, Polyquaternium 7, Polyquaternium 10, Polyquaternium 11, Polyquaternium 16, Polyquaternium 22, Polyquaternium 28, Polyquaternium 30, Polyquaternium 37, Polyquaternium 36 and Polyquaternium 46.

16. The conditioning composition according to claim 15 wherein the cationic polymer is Polyquaternium 10.

17. A method for improving hair properties comprising smoothness, combability, shine, volume and body and elasticity comprising the step of applying to the hair a composition comprising spray dried yoghurt powder and at least one cationic polymer selected from a Polyquaternium cationic compound or Guar hydroxypropyl trimonium chloride.

* * * * *